United States Patent [19]

Papenfuhs et al.

[11] Patent Number: 4,686,301

[45] Date of Patent: Aug. 11, 1987

[54] PROCESS FOR THE PREPARATION OF 2,4-DINITROPHENOL ALKOXYALKYL ETHERS

[75] Inventors: Theodor Papenfuhs; Friedrich Schophoff, both of Frankfurt am Main, Fed. Rep. of Germany

[73] Assignee: Hoechst Aktiengesellschaft, Frankfurt am Main, Fed. Rep. of Germany

[21] Appl. No.: 869,238

[22] Filed: Jun. 2, 1986

[30] Foreign Application Priority Data

Jun. 4, 1985 [DE] Fed. Rep. of Germany ....... 3519983

[51] Int. Cl.$^4$ ................. C07D 307/02; C07D 315/00; C07D 309/00; C07C 41/01
[52] U.S. Cl. .................................. 549/427; 549/497; 568/586; 568/587
[58] Field of Search ................ 568/586, 587; 549/427, 549/497, 495

[56] References Cited

U.S. PATENT DOCUMENTS 2,988,571  6/1961  MacFie et al. ................. 568/586 X

FOREIGN PATENT DOCUMENTS 634032  12/1963  Belgium .
0011048  5/1980  European Pat. Off. .
3437665  1/1986  Fed. Rep. of Germany .

*Primary Examiner*—Howard T. Mars
*Attorney, Agent, or Firm*—Connolly & Hutz

[57] ABSTRACT

Process for the preparation of compounds of the formula (I)

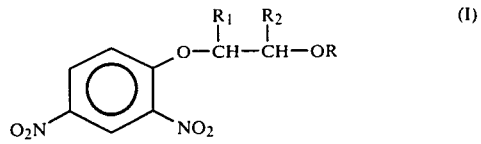

in which R denotes a $C_1$–$C_4$-alkyl radical which is optionally substituted by $C_1$–$C_4$-alkoxy groups, or a phenyl radical which can be substituted by alkyl or alkoxy groups having 1 to 4 carbon atoms or by chlorine or bromine atoms, or, together with $R_2$, denotes an alkylene bridge $-(CH_2)_n-$ in which n is the number 3 or 4, $R_1$ denotes a hydrogen atom or an alkyl radical having 1 to 4 carbon atoms, and $R_2$ represents a hydrogen atom or an alkyl radical having 1 to 4 carbon atoms, or, together with R, represents an alkylene bridge $-(CH_2)_n-$ in which n has the meaning mentioned, by reacting 2,4-dinitrochlorobenzene with an alcohol of the formula (II)

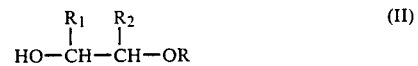

in which R, $R_1$ and $R_2$ have the meanings mentioned above, in the presence of lithium oxide or lithium hydroxide at temperatures from 0° to 5° C., if appropriate neutralizing the reaction mixture with a non-volatile, weak acid which is soluble in the reaction medium, and subsequently removing by distillation the alcohol of the formula (II), present in excess, then adding sufficient water at 20° to 80° C. for the lithium chloride formed to dissolve completely, and separating off, from the aqueous salt phase, the 2,4-dinitrophenol alkoxyalkyl ether which has separated out in a solid or liquid phase.

1 Claim, No Drawings

PROCESS FOR THE PREPARATION OF 2,4-DINITROPHENOL ALKOXYALKYL ETHERS

The invention relates to a process for the preparation of 2,4-dinitrophenol alkoxyalkyl ethers by reacting 2,4-dinitrochlorobenzene with alcohols in the presence of lithium oxide or hydroxide.

2,4-dinitrophenol alkoxyalkyl ethers of the general formula (I)

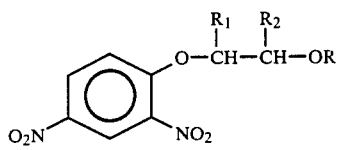

in which R denotes a $C_1$–$C_4$-alkyl radical which is optionally substituted by $C_1$–$C_4$-alkoxy groups, or a phenyl radical which can be substituted by alkyl or alkoxy groups having in each case one to four carbon atoms or by chlorine or bromine atoms, or, together with $R_2$, denotes an alkylene bridge —$(CH_2)_n$— in which n is the number 3 or 4, $R_1$ denotes a hydrogen atom or an alkyl radical having 1 to 4 carbon atoms and $R_2$ represents a hydrogen atom or an alkyl radical having 1 to 4 carbon atoms or, together with R, represents an alkylene bridge —$(CH_2)_n$— in which n has the meaning mentioned, are industrially important precursors for the preparation of azo disperse dyestuffs, such as are described, for example, in Belgian Pat. No. 634,032. Two processes have been suggested for their preparation:

1. Reacting 2,4-dinitrochlorobenzene with an alcohol of the formula (II)

in which $R_1$, $R_2$ and R have the meanings mentioned above, in the presence of sodium hydroxide (European Published Application No. 11,048).

2. Reacting 2,4-dinitrochlorobenzene with an alkali metal alcoholate of the formula (III)

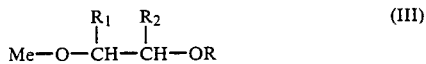

in which $R_1$, $R_2$ and R have the meanings mentioned above the Me represents an alkali metal atom (German Patent Application No. P 3,437,665.8).

The first reaction mentioned takes place with only a low degree of selectivity and, depending on the molar ratio of 2,4-dinitrochlorobenzene to the alcohol of the formula II, affords up to 10% of 2,4-dinitrophenol, which is undesirable, because it is difficult to separate and can scarcely be disposed of. Although the formation of 2,4-dinitrophenol can be reduced to values of 2–3% at molar ratios of 2,4-dinitrochlorobenzene to alcohol of the formula II of 1:~5, a decisive improvement is not achieved thereby, because, in this case too, it does not permit the use of unpurified 2,4-dinitrophenol alkoxyalkyl ether (I) as a starting material for subsequent reactions (catalytic reduction), which would be desirable, and, in addition, affords recovered alcohols of the said formula (II) containing water, which can only be freed from water by extremely involved technical processes, but which, as a result of their water content, in the absence of this step lead to a greatly increased formation of 2,4-dinitrophenol in the reaction with 2,4-dinitrochlorobenzene.

The second reaction mentioned does not suffer from these problems, but requires, as the starting material for the preparation of the alkali metal alcoholate of the said formula (III), an alkali metal, the technical handling of which necessitates special equipment and involved disposal of exit gas (hydrogen, containing solvent).

There was, therefore, a need for a technically practicable process for the preparation of 2,4-dinitrophenol alkoxyalkyl ethers which permits the reaction to be carried out without the use of an alkali metal in such a way that amounts of 2,4-dinitrophenol which would interfere with subsequent reactions are not formed, i.e. the undesirable formation of 2,4-dinitrophenol is reduced to less than 1.5%. In addition, there must be no formation of recovered alcohol of said formula (II) containing water, since this, in the event of recycling, would render the mentioned objective unachievable.

It has now been found, surprisingly, that 2,4-dinitrophenol alkoxyalkyl ethers of the general formula (I) mentioned above, containing less than 1.5% of undesirable 2,4-dinitrophenol, can be prepared in a technically simple manner by reacting 2,4-dinitrochlorobenzene with an alcohol of the formula (II)

in which $R_1$, $R_2$ and R have the meanings mentioned above, in the presence of lithium oxide or lithium hydroxide at temperatures from 0° C. to 50° C., preferably 20° C. to 40° C., if necessary neutralizing the reaction mixture with a non-volatile weak acid which is soluble in the reaction medium and subsequently removing by distillation the alcohol of the formula (II), present in excess, then adding sufficient water at 20° to 80° C., preferably 35° to 60° C., for the lithium chloride formed to dissolve completely, and separating off, from the aqueous salt phase, the 2,4-dinitrophenol alkoxyalkyl ether which separates out in a solid or liquid phase.

The lithium hydroxide can be employed in an anhydrous form or in the form of lithium hydroxide hydrate (LiOH. $H_2O$), which is cheaper.

When anhydrous lithium hydroxide is used, it is possible, by using only a slight excess of alcohol of the said formula (II), to prepare a 2,4-dinitrophenol alkoxyalkyl ether of the said formula (I) which can be employed in subsequent reactions without further purification. Since recovery of the alcohol employed is superfluous because of the virtually stoichiometric reaction of the 2,4-dinitrochlorobenzene with an alcohol of the formula (II), problems involving undesirable recovered material containing water do not arise, so that the target products of the formula (I) are accessible by the process according to the invention in a manner which is technically particularly simple and without expensive special equipment or manipulations.

If lithium hydroxide hydrate is used, the alcohol of the formula (II) must be employed in an at least 5-molar excess, relative to the 2,4-dinitrochlorobenzene employed. In the course of the recovery of the excess alcohol of the formula (II) by distillation, which is necessary in this case, a distillate containing water results, and this must, from time to time, be expensively freed from water before being re-used (fractionation in multiplate columns or entrainment distillation with non-polar solvents, for example cyclohexane or toluene), for which reason this process variant is less preferable.

In detail, the process is carried out by adding a 1-molar to 1.2-molar, preferably 1.05-molar to 1.1-molar amount of lithium compound (½ $Li_2O$ or LiOH or $LiOH.H_2O$) with stirring to a mixture of 1 mol of 2,4-dinitrochlorobenzene and a 1.2-molar to 10-molar, preferably 1.3-molar to 1.7-molar, amount of an alcohol of the formula (II) at temperatures from 0° to 50° C., preferably 20° to 40° C., in the course of 0.5 to 5 hours, preferably 1 to 2 hours, continuing stirring for 2 to 10 hours, preferably 3 to 5 hours, and, if appropriate after removing the excess alcohol of the formula (II) by distillation from the reaction mixture which has been neutralized with a non-volatile, weak acid which is soluble in the medium, such as, for example, benzoic acid, terephthalic acid or isophthalic acid, adding sufficient water at 20° to 80° C., preferably 35° to 60° C., for the lithium chloride formed to dissolve completely, and separating off, by filtration or phase separation from the aqueous salt phase, the 2,4-dinitrophenol alkoxyalkyl ether which then separates out in the form of granules or as a liquid phase.

This process gives, in a 98 to 99% yield, a product of the said formula (I) which is virtually free from 2,4-dinitrophenol and can be used without purification for subsequent reactions (for example catalytic reduction). The lithium 2,4-dinitrophenate formed (not more than 1.5%, relative to the 2,4-dinitrochlorobenzene employed) remains quantitatively dissolved in the aqueous salt phase, which, if appropriate after treatment with an adsorbent (active charcoal, a synthetic absorption resin of the XAD type or basic mineral adsorbents), can be fed to a biological effluent disposal plant.

In contrast with this, a compound of the formula (I), prepared by the process of European Published Application No. 11,048 mentioned earlier in the text, contains 3 to 6% of 2,4-dinitrophenol in the form of the sodium salt, as a result of which subsequent reactions (for example catalytic reduction) cannot be carried out without expensive purification (for example extraction by stirring several times with a 20-fold to 30-fold amount of water), and the purifying solutions also present considerable disposal problems because of their high content of 2,4-dinitrophenol.

Compared with the known processes, therefore, the process according to the invention constitutes a considerable technical advance.

The following examples are intended to illustrate the invention in greater detail without limiting its scope thereto.

EXAMPLE 1

25.2 parts of lithium hydroxide (anhydrous) are added in portions, in the course of 90 minutes, to a stirred mixture of 202.6 parts of 2,4-dinitrochlorobenzene and 116 parts of methylglycol at such a rate that the internal temperature does not exceed 35° C. The progress of the reaction is followed by HPLC (HPLC=high pressure liquid chromatography). When 2,4-dinitrochlorobenzene can no longer be detected (approx. 3–5 hours), 750 parts of water at 60° C. are added, stirring is continued for 30 minutes at 40° C., the mixture is cooled to 0°–5° C. and the 2,4-dinitro-β-methoxyethoxybenzene, which has solidified in granules, is isolated by filtration, washed with 250 parts of water and dried. This gives 237.2 parts (98% of theory) of product of melting point 52° C., in which 2,4-dinitrophenol is no longer detectable.

A content of 0.16% of 2,4-dinitrophenol can be determined by HPLC, after neutralization with dilute hydrochloric acid, in the filtrate (1100 parts), which corresponds to the formation of 1.8 parts per batch (0.98% of theory).

EXAMPLE 2

If the reaction is carried out in the manner indicated in Example 1, but 15 parts of lithium oxide are added instead of the 25.2 parts of anhydrous lithium hydroxide, the product is 239.5 parts of 2,4-dinitro-β-methoxythoxybenzene (99% of theory) of melting point 52.5° C., in which 2,4-dinitrophenol is no longer detectable.

0.06% of 2,4-dinitrophenol can be determined by HPLC in the filtrate (1100 parts) after neutralization with hydrochloric acid (=0.65 parts per batch; 0.36% of theory).

EXAMPLE 3

If the reaction is carried out in the manner indicated in Example 1, but 45.2 parts of hydrated lithium hydroxide $LiOH.H_2O$ are employed instead of the 25.2 parts of anhydrous lithium hydroxide, the product is 233.5 parts of 2,4-dinitro-β-methoxyethoxybenzene (96.5% of theory) of melting point 51.5° C., in which 0.05% of 2,4-dinitrophenol (0.12 part of 2,4-dinitrophenol; 0.06% of theory) is still present according to HPLC.

0.27% of 2,4-dinitrophenol can be detected by HPLC in the filtrate (1100 parts) after neutralization with hydrochloric acid (=3.00 parts per batch; 1.63% of theory), so that the total formation of 2,4-dinitrophenol is 3.12 parts per batch (=1.69% of theory).

EXAMPLE 4

25.2 parts of anhydrous lithium hydroxide are added, with stirring, to a mixture of 202.6 parts of 2,4-dinitrochlorobenzene and 608.8 parts of methyl glycol at a maximum of 30° C. and within the course of 30 minutes.

Stirring is continued for three hours at 25° C., until 2,4-dinitrochlorobenzene can no longer be detected by HPLC, 6.7 parts of benzoic acid are then added and the excess methylglycol is substantially removed by distillation at 100 mbar and a maximum bottom temperature of 90° C.

After cooling to 60° C., the residue is stirred with 400 parts of water at 60° C. The organic lower phase is then washed again with twice 200 parts of water at 60° C. 237.8 parts of dinitrophenol-free 2,4-dinitro-β-methoxyethoxybenzene melt (98.3% of theory) having a solidification point of 50° C. are obtained. 0.08% of 2,4-dinitrophenol (320.92 part per batch; 0.50% of theory) can be detected by HPLC in the combined aqueous phases (1112 parts).

EXAMPLE 5

If the reaction is carried out in the manner indicated in Example 4, but 45.2 parts of hydrated lithium hydroxide ($LiOH.H_2O$) are employed instead of the 25.2 parts of anhydrous lithium hydroxide, the product is 236.0 parts of 2,4-dinitro-β-methoxyethoxybenzene melt (97.5% of theory) of solidification point 49.5° C., in which 2,4-dinitrophenol is not detectable by means of HPLC. 0.15% of 2,4-dinitrophenol (=1.70 parts per batch; 0.92% of theory) can be detected by HPLC in the combined aqueous phases (1130 parts).

EXAMPLE 6

25.0 parts of anhydrous lithium hydroxide are added in portions in the course of one hour, with stirring and at a temperature not higher than 30° C., to a mixture of 202.6 parts of 2,4-dinitrochlorobenzene and 126 parts of ethylglycol.

Stirring is then continued until dinitrochlorobenzene can no longer be detected in the reaction mixture by HPLC (3–5 hours), 750 parts of water at 50° C. are then added, stirring is continued for 30 minutes at 50° C. and the organic lower layer is separated off. It is washed by extraction by stirring with twice 250 parts of water at 50° C. Drying in vacuo gives 251.0 parts of 2,4-dinitro-$\beta$-ethoxyethoxybenzene (98.0% of theory) which is liquid at room temperature and in which 2,4-dinitrophenol can no longer be detected by HPLC.

0.14% of 2,4-dinitrophenol (=1.82 parts per batch; 0.99% of theory) can be detected by HPLC in the combined aqueous phases (1200 parts) after neutralization with dilute hydrochloric acid.

EXAMPLES 7–14

If the reaction is carried out in the manner described in Example 6, but the ethylglycol is replaced by aliquot amounts of the alcohols of the general formula (II) mentioned, indicated in the table below, the corresponding 2,4-dinitrophenol alkoxyalkyl ethers of the general formula (I) mentioned are obtained in the reaction time stated and in the yield mentioned in the table. 2,4-dinitrophenol cannot be detected by HPLC in any of these products isolated, which have been prepared in accordance with the invention.

The amount of 2,4-dinitrophenol found by HPLC analysis in the aqueous phases is also shown in the table (in % of theory).

TABLE

| Example | Alcohol (II) | Reaction time | Yield | Melting point | Formation of 2,4-dinitrophenol |
|---|---|---|---|---|---|
| 7 | n-butylglycol | 5 | 97.9% | — | 1.10% |
| 8 | methyldiglycol | 5 | 98.1% | 44–45° C. | 1.1% |
| 9 | ethyldiglycol | 8 | 97.6% | — | 2.08% |
| 10 | n-butyldiglycol | 10 | 97.1% | — | 1.21% |
| 11 | i-propylglycol | 7 | 97.8% | — | 0.9% |
| 12 | phenylglycol | 8 | 98.0% | 61–62° C. | 0.8% |
| 13 | 3-methoxybutanol | 8 | 97.2% | 42–43° C. | 1.3% |
| 14 | tetrahydrofurfuryl alcohol | 6 | 98.2% | 53–54° C. | 1.1% |

If no melting point is indicated, the reaction products obtained (corresponding to the formula (II) are liquid at room temperature.

COMPARISON EXAMPLE (IN ACCORDANCE WITH EUROPEAN PUBLISHED APPLICATION NO. 11,048)

If the anhydrous lithium hydroxide in Example 1 according to the invention is replaced by 42 parts of sodium hydroxide (anhydrous, in the form of tablets and prills) and if the reaction is carried out in other respects in the manner indicated, the product is 229.5 parts of a granulated reaction product of melting point 45°–48° C., which, according to HPLC, contains 3% of 2,4-dinitrophenol (6.9 parts; 3.75% of theory). The yield of 2,4-dinitro-$\beta$-methoxyethoxybenzene is, accordingly, 222.6 parts, corresponding to 92.0% of theory.

0.59% of 2,4-dinitrophenol can be detected by HPLC in the filtrate (1100 parts) after acidification with dilute hydrochloric acid. This corresponds to the formation of a further 6.5 parts (3.53% of theory) of 2,4-dinitrophenol, so that the total formation of 2,4-dinitrophenol is 13.4 parts per batch (7.28% of theory).

We claim:

1. A process for the preparation of 2,4-dinitrophenol alkoxyalkyl ethers of the formula (I)

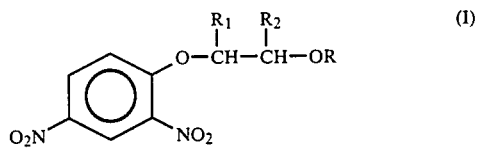

in which R denotes a $C_1$–$C_4$-alkyl radical which is optionally substituted by $C_1$–$C_4$-alkoxy groups, or a phenyl radical which can be substituted by alkyl or alkoxy groups having in each case 1 to 4 carbon atoms or by chlorine or bromine atoms, or, together with $R_2$, denotes an alkylene bridge —$(CH_2)_n$— in which n is the number 3 or 4, $R_1$ denotes a hydrogen atom or an alkyl radical having 1 to 4 carbon atoms, and $R_2$ represents a hydrogen atom or an alkyl radical having 1 to 4 carbon atoms, or, together with R, represents an alkylene bridge —$(CH_2)_n$— in which n has the meaning mentioned, which comprises reacting 2,4-dinitrochlorobenzene with an alcohol of the formula (II)

in which R, $R_1$ and $R_2$ have the meanings mentioned above, in the presence of lithium oxide or lithium hydroxide at temperatures from 0° to 50° C., if appropriate neutralizing the reaction mixture with a non-volatile, weak acid which is soluble in the reaction medium, and subsequently removing by distillation the alcohol of the formula (II), present in excess, then adding sufficient water at 20° to 80° C. for the lithium chloride formed to dissolve completely, and separating off, from the aqueous salt phase, the 2,4-dinitrophenol alkoxyalkyl ether which has separated out in a solid or liquid phase.

* * * * *